US009560961B2

(12) United States Patent
Inoue

(10) Patent No.: US 9,560,961 B2
(45) Date of Patent: Feb. 7, 2017

(54) OPTICAL COHERENCE TOMOGRAPHY APPARATUS, CONTROL METHOD FOR OPTICAL COHERENCE TOMOGRAPHY APPARATUS, AND NON-TRANSITORY TANGIBLE MEDIUM

(71) Applicant: CANON KABUSHIKI KAISHA, Tokyo (JP)

(72) Inventor: Hiroyuki Inoue, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/257,168

(22) Filed: Apr. 21, 2014

(65) Prior Publication Data
US 2014/0327916 A1    Nov. 6, 2014

(30) Foreign Application Priority Data

May 1, 2013   (JP) .................. 2013-096400

(51) Int. Cl.
  *G01B 11/02*      (2006.01)
  *A61B 3/10*       (2006.01)
  *G01B 9/02*       (2006.01)
(52) U.S. Cl.
  CPC ........... *A61B 3/102* (2013.01); *G01B 9/02091* (2013.01)
(58) Field of Classification Search
  CPC ............ G01B 9/02091; G01B 9/02085; G01B 9/02089
  USPC ................................. 356/479, 497
  See application file for complete search history.

(56) References Cited

U.S. PATENT DOCUMENTS

| 8,794,761 B2 | 8/2014 | Kobayashi |
| 2008/0100612 A1* | 5/2008 | Dastmalchi et al. ......... 345/418 |
| 2011/0032479 A1* | 2/2011 | Utsunomiya ................ 351/206 |
| 2011/0205490 A1* | 8/2011 | Murata et al. ............... 351/206 |

(Continued)

FOREIGN PATENT DOCUMENTS

| CN | 102264282 A | 11/2011 |
| JP | 2011-092290 A | 5/2011 |

(Continued)

OTHER PUBLICATIONS

Oct. 7, 2014 European Search Report in European Patent Appln. No. 14166149.6.

(Continued)

*Primary Examiner* — Jonathan Hansen
(74) *Attorney, Agent, or Firm* — Fitzpatrick, Cella, Harper & Scinto

(57) ABSTRACT

Provided is an optical coherence tomography apparatus expected to facilitate observation of reliable analyzed image data to improve inspection efficiency. The tomography apparatus includes: an acquisition unit configured to acquire a tomographic image of an object to be inspected; an identifying unit configured to identify an image display area corresponding to a part to be inspected of the object to be inspected in the tomographic image; a determination unit configured to determine a significant area and a non-significant area based on a positional relationship between a periphery of the image display area and the tomographic image; and a display control unit configured to control a display unit to display image data based on the tomographic image and data concerning the non-significant area together in a designated display form.

32 Claims, 13 Drawing Sheets

(56) References Cited

U.S. PATENT DOCUMENTS

2011/0228222 A1 9/2011 Kobayashi
2012/0218520 A1 8/2012 Inoue
2013/0188129 A1 7/2013 Inoue
2013/0188130 A1 7/2013 Inoue

FOREIGN PATENT DOCUMENTS

| JP | 2012-071113 A | 4/2012 |
|---|---|---|
| WO | 2007/028531 A1 | 3/2007 |
| WO | 2011/018950 A1 | 2/2011 |
| WO | 2011/114685 A1 | 9/2011 |

OTHER PUBLICATIONS

Aug. 4, 2015 Chinese Official Action in Chinese Patent Appln. No. 201410184183.7.

* cited by examiner

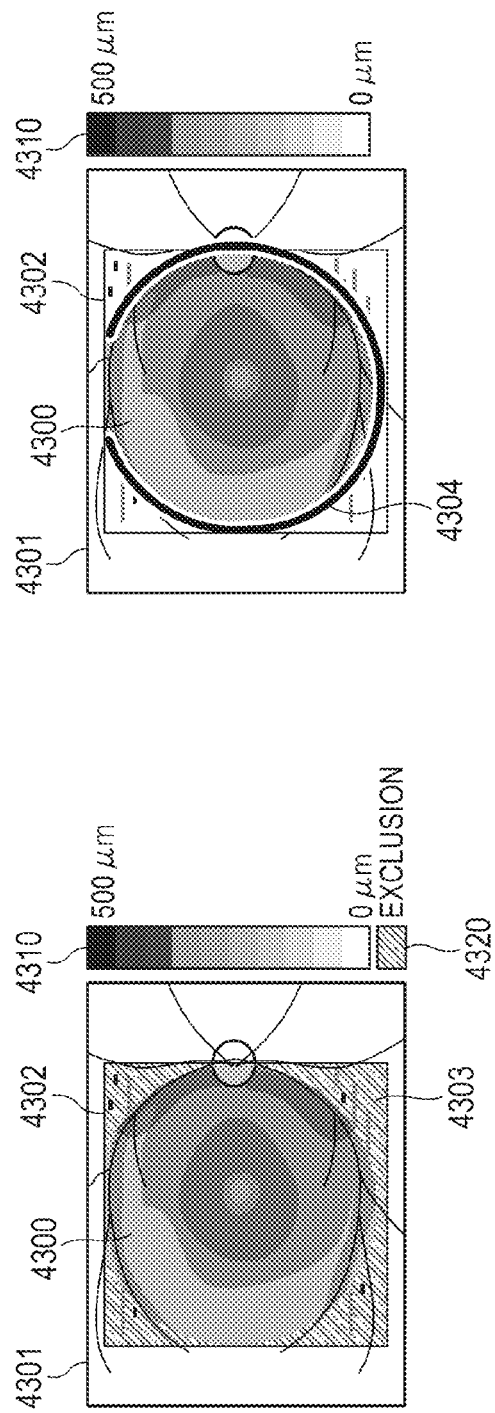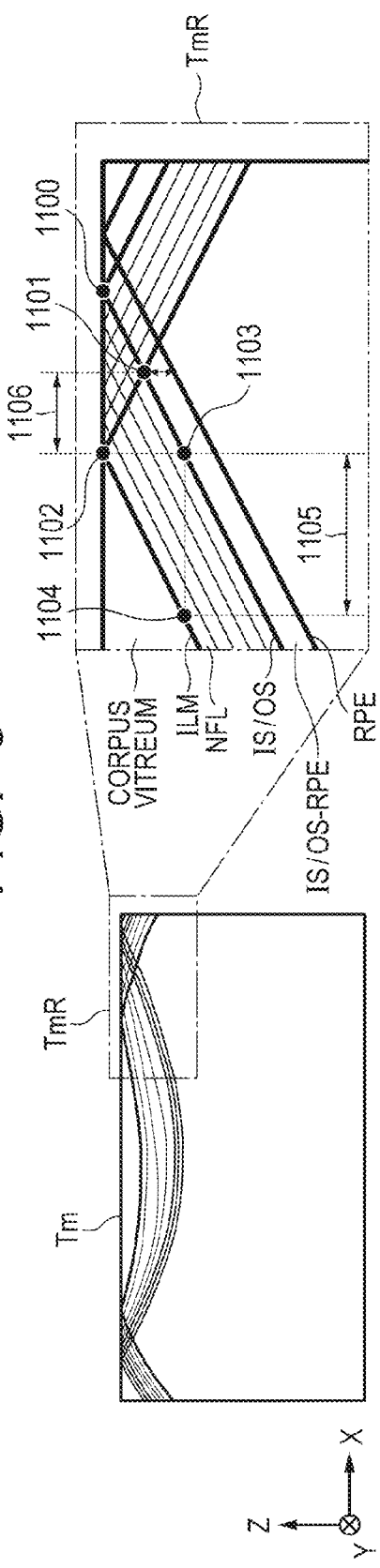

OPTICAL COHERENCE TOMOGRAPHY APPARATUS, CONTROL METHOD FOR OPTICAL COHERENCE TOMOGRAPHY APPARATUS, AND NON-TRANSITORY TANGIBLE MEDIUM

BACKGROUND OF THE INVENTION

Field of the Invention

The present invention relates to an optical coherence tomography apparatus as represented by, for example, an ophthalmologic device, avid to a control method for the optical coherence tomography apparatus and a non-transitory tangible medium.

Description of the Related Art

Currently, there are various types of ophthalmologic devices using an optical device. For instance, as an optical device for observing an eye, there are used various devices such as an anterior ocular segment imaging device, a fundus camera, and a confocal laser scanning ophthalmoscope (scanning laser ophthalmoscope: SLO). In particular, an optical tomographic imaging apparatus, which performs optical coherence tomography (OCT) utilizing an interference phenomenon of multi-wavelength light, is an apparatus capable of obtaining a tomographic image of a sample with high resolution. For this reason, the optical tomographic imaging apparatus is becoming an indispensable apparatus as an ophthalmologic device tor a specialist of retina in the outpatient field. In addition, the optical tomographic imaging apparatus is used not only for ophthalmologic use but also for an endoscope or the like. This apparatus is hereinafter referred to as "OCT apparatus". The OCT apparatus is widely used for acquiring a tomographic image of a retina of a fundus or a tomographic image of an anterior ocular segment such as a cornea of an eye to be inspected in ophthalmologic diagnosis or the like.

The OCT apparatus is capable of splitting measuring light having low coherence into reference light and measuring light, and irradiating an object to be inspected with the measuring light to cause return light from the object to be inspected to interfere with the reference light, to thereby measure a layer of the object to be inspected from spectrum information of interference light. As to the current OCT apparatus, a spectrum domain OCT (SD-OCT), which can acquire information on the object to be inspected in a depth direction from the above-mentioned spectrum information on interference light, is used in general. In the present invention, the SD-OCT apparatus is hereinafter referred to simply as "OCT apparatus".

The OCT apparatus, which is capable of acquiring a high resolution tomographic image by scanning a sample with measuring light, acquires a two-dimensional image by one-dimensional scanning of a specific area with the measuring light. Further, a three-dimensional image (volume data) is acquired by repeating the one-dimensional scanning for acquiring the two-dimensional tomographic image while shifting a position.

Here, it is known that the retina of a human eye includes a plurality of layers. In ophthalmological diagnosis, radiographic image interpretation of the layer structure is made or a state of a lesioned part is checked based on the volume data. In addition, in volume image data of the retina, in order to check a state of a lesioned part, it is effective to display a tomographic image, to analyze a layer structure image of the retina, and to display a layer thickness graph, a layer thickness map, or the like (see Japanese Patent Application Laid-Open No. 2012-071113). Further, it is also effective to compare a calculated layer thickness with layer thickness data of a healthy eye (normative data base (NDB)) for checking a state of a lesioned part.

However, it is known that when the spectrum information is used for acquiring a tomographic image of the object to be inspected, there is generated a folded image of a normal tomographic image with respect to a position called a gate at which a measuring optical path and a reference optical path are equal to each other, due to characteristics of Fourier transform performed in the calculation thereof. Further, when the tomographic image of the object to be inspected crosses the gate position, the normal tomographic image and the folded tomographic image are overlaid to become a double image.

When the tomographic image is a double image, it is difficult to distinguish a layer structure of the sample by image analysis. For this reason, layer thickness analysis data of the double imaging area, may not be appropriately provided to a user. Therefore, in Japanese Patent Application Laid-open No. 2011-092290, there is disclosed an ophthalmologic device in which a warning is issued when a tomographic image of an object to be inspected is formed outside an appropriate photographable area in order to prevent photographing an image in a state where the folded image is overlaid on the normal tomographic image.

However, even when the ophthalmologic device disclosed in Japanese Patent Application Laid-open No. 2011-092290 is used, the user may perform photography in a state where a folded image is generated. This is because the user may perform photography with a focused part intentionally positioned to be close to the gate position because the tomographic image becomes more blurred due to a decrease of signal intensity or the like as the focused part becomes distant from the gate position. In addition, because the retina of a human eye does not have a flat plans but has a curved shape, the tomographic image may cross the gate position to generate the folded image in an area distant from the focused part. Further, when the retina has a large curvature due to excessive myopia or the like, it may be difficult to photograph the entire retina in a state in which no folded image is generated.

SUMMARY OF THE INVENTION

Therefore, in view of the above-mentioned problems, it is an object of the present invention to provide an optical coherence tomography apparatus that is expected to appropriately present a user with layer thickness data to improve inspection efficiency can be expected.

In order to solve the above-mentioned problems, according to the present invention, there is provided an optical coherence tomography apparatus, including: an acquisition unit configured to acquire a tomographic image of an object to be inspected; an identifying unit configured to identify an image display area corresponding to a part to be inspected of the object to be inspected in the tomographic image; a determination unit configured to determine a significant area and a non-significant area based on a positional relationship between a periphery of the image display area and the tomographic image; and a display control unit configured to control a display unit to display image data based on the tomographic image and data concerning the non-significant area together in a designated display form.

The optical coherence tomography apparatus according to one embodiment of the present invention can clearly show an area in which a folded image may affect analyzed image data, and hence the user can pay attention only to analyzed image data with high reliability so that analysis efficiency can be improved.

Further features of the present invention will become apparent from the following description of exemplary embodiments with reference to the attached drawings.

BRIEF DESCRIPTION OF THE DRAWINGS

FIGS. 7A and 7B are explanatory diagrams of various examples of the layer thickness map display according to the present invention.

FIG. 8 is an explanatory diagram of a method of identifying a significant area of IS/OS-RPE.

DESCRIPTION OF THE EMBODIMENTS

Main Body Structure

Figure 2A:
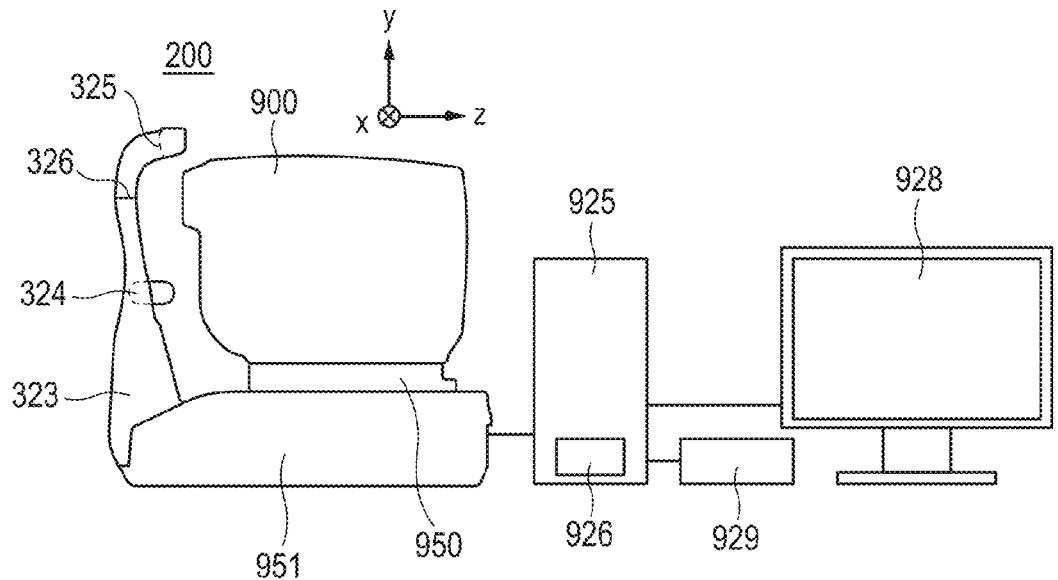
FIG. 2A is a general schematic diagram of an optical coherence tomography apparatus according to the present invention.

FIG. 2A is a side view of an optical tomographic imaging apparatus according to an embodiment of the present invention. An optical coherence tomography apparatus 200 includes an acquisition portion (measuring optical system) 900 for acquiring an anterior ocular segment image, and a two-dimensional image and a tomographic image of an eye to be inspected, and a stage portion 950 as a moving portion capable of moving the image acquisition portion 900 in X, Y, and Z directions using a motor (not shown). The optical coherence tomography apparatus 200 also includes a base portion 951 in which a spectroscope described later is disposed.

As described later in detail, the image acquisition portion 900 scans an object to be inspected with light for acquiring an image of the object to be inspected, so as to photograph the object to be inspected to acquire an image of the object to be inspected.

A personal computer 925 constructs tomographic images and controls the stage portion, alignment operation, and the like. Further, as described later, the personal computer 925 identifies an imaging area, analyzes layer structures, identifies a significant area, generates analyzed image data, and controls display of a monitor. A hard disk 926 is a memory portion for storing a tomographic imaging program and reference layer thickness data in advance and also works as a patient information memory portion for storing patient information and various photographed data.

A monitor 928 serves as a display portion, and an input portion 929 gives an instruction to the personal computer. Specifically, the input portion 929 includes a keyboard and a mouse. In other words, the monitor 928 is a single common monitor for displaying a photography screen and a report screen in a time division manner, which are described later. The monitor 928 is disposed not on the image acquisition portion 900 side but on the personal computer 925 side.

A face support 323 includes a chin rest 324 capable of being moved up and down by a motor (not shown), a forehead rest 325, and an eye height line 326 disposed at a center of a movement area in the height direction of an objective lens described later. The face of a subject is fixed by placing the chin of the subject on the chin rest 324 and pushing the forehead to the forehead rest 325 so that a height of the eye of the subject may be substantially the same as a height of the eye height line 326. Thus, the eye to be inspected is roughly positioned at the acquisition portion 900.

Block Diagram

Figure 2B:
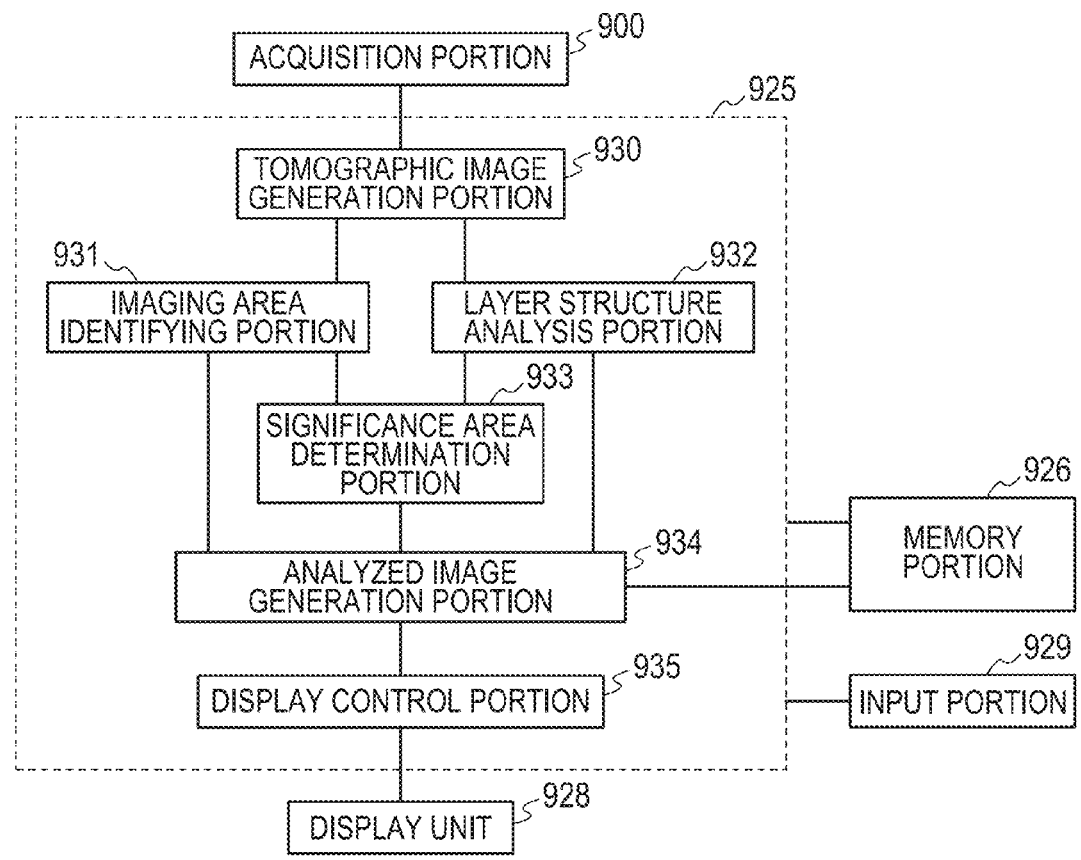
FIG. 2B is a block diagram of the optical coherence tomography apparatus according to the present invention.

A block diagram of this embodiment is described with reference to FIG. 2B. Details of each operation are described later.

A tomographic image generation portion 930 generates a tomographic image based on a signal acquired by the acquisition portion 900 from interference light as described later.

An imaging area identifying portion 931 analyzes the tomographic image formed by the tomographic image generation portion 930 so as to identify an imaging area corresponding to a predetermined part of an object to be inspected. The imaging area means an area of an image displayed on the monitor 928, and a size of the imaging area is uniform, for example. The imaging area identifying portion 931 corresponds to an identifying unit in the present invention, which identifies an imaging area that is a part corresponding to a part to be inspected of the object to be inspected in the tomographic image, which requires inspection.

A layer structure analysis portion 932 analyzes the tomographic image formed by she tomographic image generation portion 930 and distinguishes a layer structure of the object to be inspected. The layer structure analysis portion 932 corresponds to an analysis unit in the present invention.

A significant area determination portion 933 sets the significant area based on the imaging area formed by the imaging area identifying portion 931 and the layer structure formed by the layer structure analysis portion 932. Here, the significant area is a feature structure of the present invention, and details thereof are described later. The significant area determination portion 933 corresponds to a determination unit configured to determine the significant area and a non-significant area based on a positional relationship between an area peripheral part of the imaging area and the tomographic image in the present invention. Further, details of this positional relationship are described later.

An analyzed image generation portion 934 generates the analyzed image data based on the imaging area formed by the imaging area identifying portion 931, the layer structure formed by the layer structure analysis portion 932, the significant area formed by the significant area determination portion 933, and the reference layer thickness data stored in the memory portion 926. Here, the analyzed image data include a layer thickness map displaying layer thicknesses of the object to be inspected as a color map, and sector layer thickness data displaying average value data of specific layer thicknesses in areas (sectors) by dividing the object to be inspected into some areas. The analyzed image generation portion 934 corresponds to a generation unit in the present invention.

The display control unit 935 controls the monitor 928 as a display unit to display the analyzed image data generated by the analyzed image generation portion 934. In addition, as described later, the display control unit designates a display form in which the image data based on the tomographic image and data concerning the non-significant area are displayed together, and controls the monitor 928 to display.

Structures of Measuring Optical System and Spectroscope

Figure 2C:
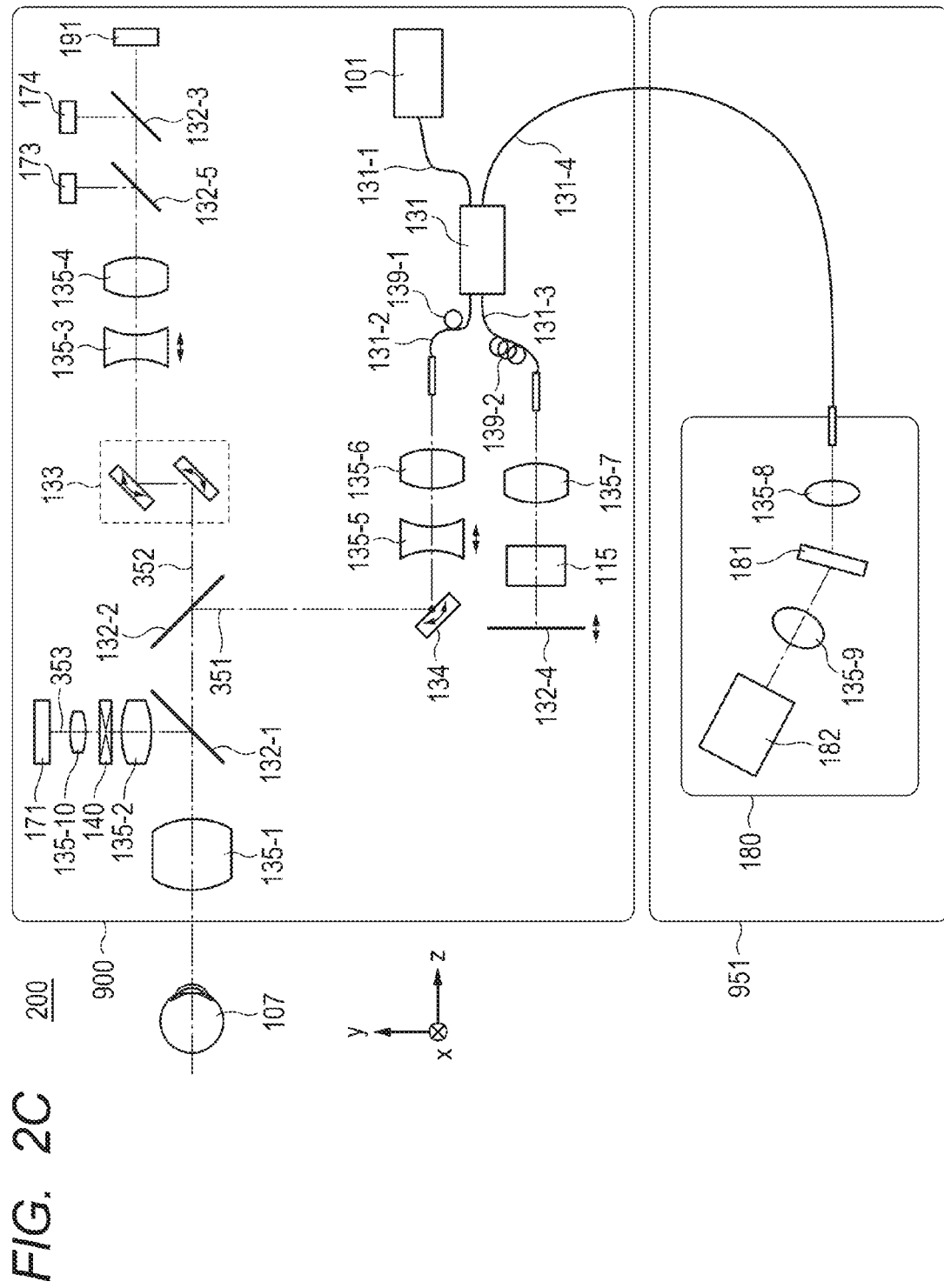
FIG. 2C is an explanatory diagram of a measuring optical system as an image acquisition portion of the optical coherence tomography apparatus according to the present invention.

Structures of the measuring optical system and the spectroscope according to this embodiment are described with reference to FIG. 2C. First, the inside of the image acquisition portion 900 is described. An objective lens 135-1 is disposed to be opposed to an eye to be inspected 107, and a first dichroic mirror 132-1 and a second dichroic mirror 132-2 are disposed on an optical axis of the objective lens 135-1. Those dichroic mirrors split an optical path into an optical path 351 for an OCT optical system, an optical path 352 for a fixation target and an SLO optical system for observation of the eye to be inspected and acquisition of a two-dimensional image thereof, and an optical path 353 for anterior ocular segment observation, in accordance with the wavelength band.

The optical path 352 for the SLO optical system and the fixation target includes an SLO scanning unit 133, lenses 135-3 and 135-4, a mirror 132-5, a third dichroic mirror 132-3, a photodiode 173, an SLO light source 174, and a fixation target 191. The mirror 132-5 is a perforated mirror or a prism on which a hollow mirror is formed by vapor deposition, so as to separate illumination light of the SLO light source 174 from return light from the eye to be inspected. The third dichroic mirror 132-3 separates an optical path into an optical path of the SLO light source 174 and an optical path of the fixation target 191 in accordance with the wavelength band. The SLO scanning unit 133 deflects the light beams emitted from the SLO light source 174 and the fixation target 191 to scan the eye to be inspected 107. The SLO scanning unit 133 includes an X scanner for scanning in an X direction and a Y scanner for scanning in a Y direction. In this embodiment, the X scanner is formed of a polygon mirror for high speed scanning, and the Y scanner is formed of a galvanic mirror. The lens 135-3 is driven by a motor (not shown) for the SLO optical system and for focusing on the fixation target. The SLO light source 174 emits light having a wavelength of approximately 780 nm. The photodiode 173 detects return light from the eye to be inspected. The fixation target 191 emits visible light so as to urge the subject to stare.

The light emitted from the SLO light source 174 is reflected by the third dichroic mirror 132-3, passes through the mirror 132-5, the lenses 135-4 and 135-3, and is deflected by the SLO scanning unit 133 to scan the eye to be inspected 107. The return light from the eye to be inspected 107 propagates backward along the same path as the projection light, and is reflected by the mirror 132-5 so as to be guided to the photodiode 173. The light of the fixation target 191 passes through the third dichroic mirror 132-3 and the mirror 132-5, and lenses 135-4 and 135-3, and is deflected by the SLO scanning unit 133 so as to scan the eye to be inspected 107. In this case, the fixation target 191 is blinked in accordance with a movement of the SLO scanning unit so as to form an arbitrary shape at an arbitrary position on the eye to be inspected 107, and hence the subject is urged to stare.

In the optical path 353 for anterior ocular segment observation, there are disposed lenses 135-2 and 135-10, a split prism 140, and an anterior ocular segment observation CCD 171 for detecting infrared light. This CCD 171 is sensitive to a wavelength of illumination light for anterior ocular segment observation (not shown), specifically a wavelength of approximately 970 nm. The split prism 140 is disposed at a position conjugate with a pupil of the eye to be inspected 107, and it is possible to detect a distance of the acquisition portion 900 in the Z direction (front and back direction) with respect to the eye to be inspected 107 as a split image of the anterior ocular segment.

As described above, the optical path 331 of the OCT optical system constructs the OCT optical system and is used for photographing a tomographic image of the eye to be inspected 107. More specifically, the optical path 351 is used for acquiring an interference signal for forming a tomographic image. An XY scanner 134 is used for scanning the eye to be inspected with light. The XY scanner 134 is illustrated as a single mirror but is formed of galvano mirrors for scanning in two directions of X and Y axes.

Lenses 135-5 and 135-6 are disposed. The lens 135-5 is driven by a motor (not shown) in order to focus light from an OCT light source 101 emitted from a fiber 131-2 connected to an optical coupler 131 on the eye to be inspected 107. By this focusing, the return light from the eye to be inspected 107 simultaneously forms a spot image at an end of the fiber 131-2 and enter the fiber 131-2.

Next, configurations of an optical path from the OCT light source 101, a reference optical system, and the spectrometer are described. The configurations include the OCT light source 101, a reference mirror 132-4, a dispersion compensation glass 115, the optical coupler 131, optical fibers 131-1 to 131-4 in a single mode connected to the optical coupler 131 to be integrated, a lens 135-7, and a spectrometer 180.

The above-mentioned components construct a Michelson interferometer. The light emitted from the OCT light source 101 is split into measuring light on the optical fiber 131-2 side and reference light on the optical fiber 131-3 side through the optical fiber 131-1 via the optical coupler 131. The measuring light illuminates the eye to foe inspected 107 to be observed through the optical path 351 of the OCT optical system described above and reaches the optical coupler 131 through the same optical path due to reflection and scattering by the eye to be inspected.

The optical coupler 131 combines the measuring light with the reference light to form interference light. In this case, interference occurs when an optical path length of the measuring light and an optical path length of the reference light become substantially equal to each other. The reference mirror 132-4 is held so as to be adjusted in an optical axis direction by a motor and a drive mechanism (not shown) and is capable of adjusting the optical path length of the reference light to that of the measuring light varying depending on the eye to be inspected 107. The interference light is guided to the spectrometer 180 through the optical fiber 131-4.

Further, a polarization adjusting portion 139-1 is provided for the measuring light in the optical fiber 131-2. A polarization adjusting portion 139-2 is provided for the reference light in the optical fiber 131-3. Those polarization adjusting portions each have a plurality of parts in which the optical fiber is looped several times. This looped part is rotated about the longitudinal direction of the fiber to twist the fiber. In this manner, the polarization state of each of the measuring light and the reference light can be adjusted and matched to each other.

The spectrometer 180 includes lenses 135-8 and 135-9, a diffraction grating 181, and a line sensor 182. The interference light emitted from the optical fiber 131-4 is collimated through the lens 135-8 and dispersed by the diffraction grating 181 to form an image on the line sensor 182 by the lens 135-9.

The OCT optical system described above corresponds to an acquisition unit of the present invention, which illuminates the object to be inspected with measuring light so as to acquire a tomographic image.

Next, the periphery of the OCT light source 101 is described. The OCT light source 101 is a super luminescent diode (OLD) that is a typical low coherent light source. Light emitted from the light source 101 has a central wavelength of 855 nm and a wavelength band width of about 100 nm. In this case, the band width influences a resolution in an optical axis direction of a tomographic image to be acquired, and hence, is an important parameter.

Although the SLD is selected in this embodiment, the type of the OCT light source 101 is not particularly limited as long as the light source is capable of emitting low coherent light, and amplified spontaneous emission (ASE) or the like may also be used. Considering the measurement or an eye, near-infrared light is suitable for the central wavelength. Further, it is desired that the central wavelength be a shortest possible wavelength because the central wavelength influences a resolution in a lateral direction of a tomographic image to be acquired. For both the reasons, the central wavelength is set to 855 nm.

Although the Michel son interferometer is used as an interferometer in this embodiment, a Mach-Zehnder interferometer may be used. It is desired that the Mach-Zehnder interferometer be used in the case where an optical amount difference between the measuring light and the reference light is large, and the Michelson interferometer be used in the case where the optical amount difference is relatively small.

With the structure described above, a tomographic image of the eye to be inspected can be acquired, and it is possible to acquire a two-dimensional image of the eye to be inspected having high contrast even with near-infrared light.

Photography Method of Tomographic Image

A photography method of a tomographic image using the optical coherence tomography apparatus 200 is described. The optical coherence tomography apparatus 200 can photograph a tomographic image of a predetermined section of the eye to be inspected 107 by controlling the XY scanner 134. Here, a locus of tomographic image acquiring light for scanning inside the eye to be inspected is referred to as "scan pattern". As this scan pattern, for example, there is a cross scan in the shape of a cross vertically and horizontally with respect to one center point, or a 3D scan in which the entire area is scanned and filled so as to acquire a three-dimensional tomographic image (volume image) as a result. When detailed observation of a specific part is intended, the cross scan is suitable. When observation of a layer structure and a layer thickness of the entire retina is intended, the 3D scan is suitable.

A photography method for the case of performing the 3D scan is now described. First, scanning is performed with the measuring light in the X direction as illustrated in the diagram, and a predetermined photographing number of information from a photography area of the eye to be inspected in the X direction are photographed by the line sensor 182. A brightness distribution on the line sensor 182 obtained at a certain position in the X direction is processed by fast Fourier transform (FFT), and the linear brightness distribution obtained by the FFT is converted into density information to be displayed on the monitor 928. This is referred to as "A-scan image".

In addition, a two-dimensional image in which a plurality of A-scan images are arranged is referred to as "B-scan image". After photographing the plurality of A-scan images for constructing one B-scan image, the scanning positron in the Y direction is shifted and the scanning in the X direction is performed again so as to acquire a plurality of B-scan images.

The plurality of B-scan images, or a three-dimensional image (volume data) constructed of the plurality of B-scan images is displayed on the monitor 928 as described below, and hence can be used by an examiner for diagnosis of the eye to be inspected. Here, there is described an example in which the plurality of B-scan images in the X direction are acquired so that a three-dimensional image is acquired. However, it is possible to acquire the three-dimensional image by acquiring a plurality of B-scan images in the Y direction.

In this case, due to fundamental characteristics of Fourier transform, there is formed a tomographic image having a symmetric shape with respect to a specific position, namely a gate position at which the measuring optical path length and the reference optical path length are equal to each other. In addition, a periodical tomographic image with respect to the gate position is formed. Therefore, in order to form a tomographic image that can be easily observed by the examiner, it is important to cut and display the specific area (imaging area).

Structure of Capture Screen

Figure 3:
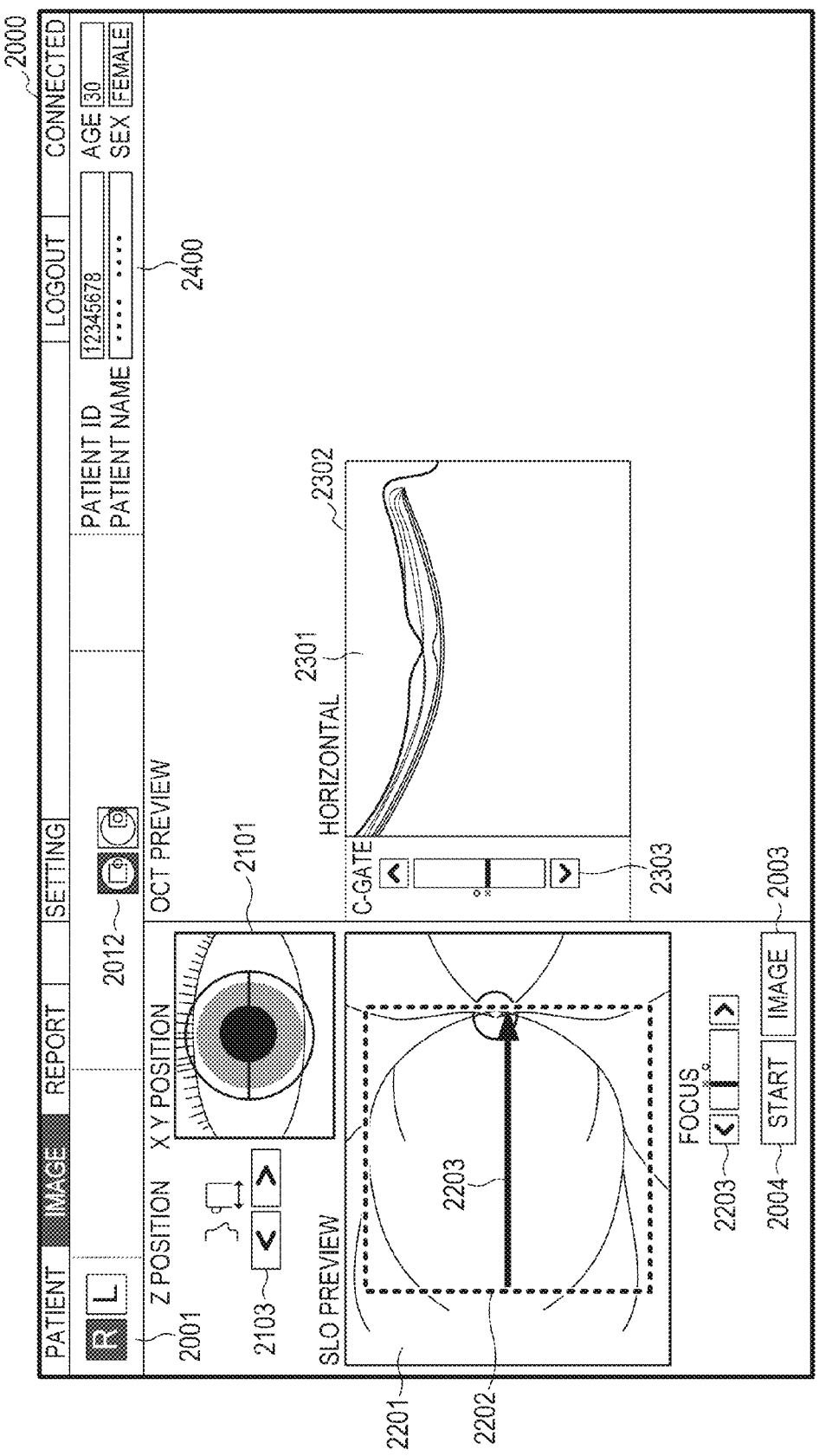
FIG. 3 is an explanatory diagram of an imaging screen which displays a real-time image (moving image) before photographing by the optical coherence tomography apparatus according to the present invention.

With reference to FIG. 3, a capture screen 2000 according to this embodiment is described. The capture screen 2000 is a screen for various settings and adjustments for acquiring a desired image of the eye to be inspected, and is a screen displayed on the monitor 928 before photography.

A patient information display portion 2400 displays information of the patient that is to be photographed on the screen, namely a patient ID, a patient name, an age, and a sex, for example. A button 2001 is used for switching between the left eye and the right eye to be inspected. When an L button or an R button is pressed, the image acquisition portion 900 is moved to an initial position of the left eye or the right eye. An anterior ocular segment observation screen 2101 is acquired by the CCD 171 for observing an anterior ocular segment. When an arbitrary point on the anterior ocular segment observation screen 2101 is clicked by a mouse, the image acquisition portion 900 is moved so that the clicked point becomes the center of the screen, and hence the image acquisition portion 900 and the eye to be inspected 107 are aligned to each other. A scan pattern display screen 2012 displays an outline of the scan pattern to be used in photography. A two-dimensional image display screen 2201 of the eye to be inspected is acquired by the photodiode 173, and a tomographic image display screen 2301 is used for checking the acquired tomographic image. When a start button 2004 is pressed, acquisition of the tomographic image and the two-dimensional image is started, and acquired images of the eye to be inspected are displayed in real time in the two-dimensional image display screen 2201 and the tomographic image display screen 2301. In this case, a frame 2202 displayed in the two-dimensional image display screen 2201 indicates an area of acquiring the tomographic image in the photography. In addition, a horizontal arrow line 2203 at the center portion in the vertical direction indicates a position and a scanning direction on the eye to be inspected whose tomographic image is acquired and displayed on the tomographic image display screen 2301.

Here, an outer frame 2302 of the tomographic image display screen 2301 indicates an imaging area in the present invention. The left side and the right side of the imaging area 2302 in the diagram are the same boundaries as the scan area 2202. The upper side is a position (gate position) at which the measuring optical path length and the reference optical path length are equal to each other, and the lower side is a position apart from the upper side by a predetermined length.

A slider disposed at a vicinity of each image is used for adjustment. A slider 2103 is used for adjusting a position of the acquisition portion in the Z direction with respect to the eye to be inspected, a slider 2203 is used for focus adjustment, and a slider 2303 is used for adjusting a position of a coherence gate. The focus adjustment is an adjustment for focusing on a fundus by moving the lenses 135-3 and 135-5 in the illustrated direction. The coherence gate adjustment is an adjustment of moving the reference mirror 132-4 in the illustrated direction so that the tomographic image is observed at a desired position on the tomographic image display screen. Thus, because an optical path length difference between the tomographic image and the reference optical path in the OCT optical system is changed, the tomographic image in the tomographic image display screen 2301 moves in an up and down direction. The examiner can identify the imaging area so that the tomographic image, more specifically, the part to be inspected is positioned at a desired position in the tomographic image display screen.

By this adjustment operation, the examiner creates a state in which an optimal photography can be performed. A photography button 2003 is pressed to perform desired photography after various adjustments are completed.

Structure of Report Screen

Figure 4:
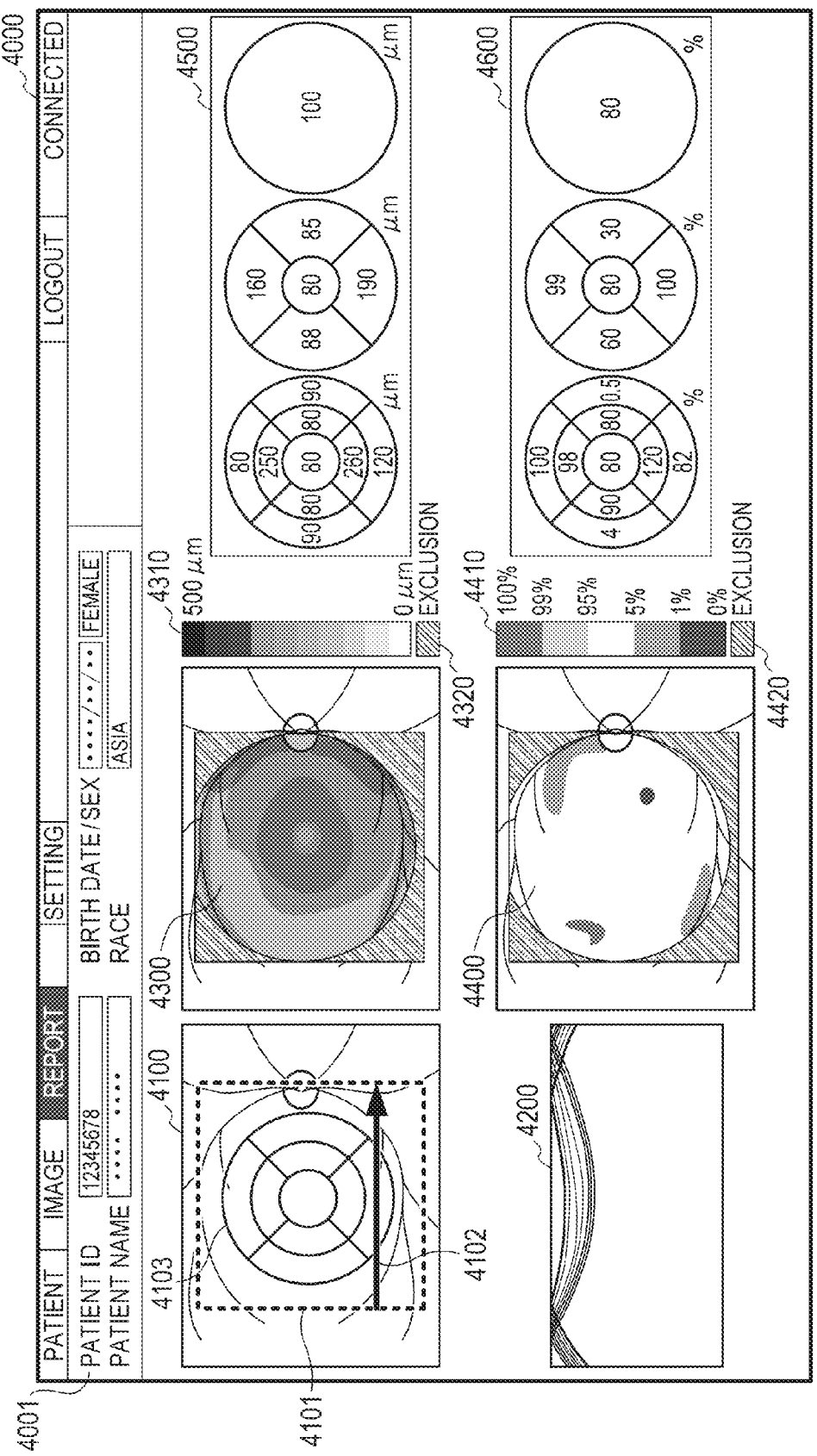
FIG. 4 is an explanatory diagram of a report screen for displaying a detailed tomographic image of the optical coherence tomography apparatus according to the present invention.

With reference to FIG. 4, a report screen 4000 according to this embodiment is described. The report screen 4000 is a screen displayed on the monitor 928 and is a screen for checking the photographed image of the eye to be inspected and the image analysis data in detail.

A patient information display portion 4001 displays information on the patent including, for example, a patient ID, a patient name, a date of birth, a sex, and a race of the patient displayed on this screen. A two-dimensional image display screen 4100 displays a projection image as an image of the eye to be inspected that is reconstructed or restructured from an SLO image or the acquired tomographic image. A tomographic image display screen 4200 displays the acquired tomographic image. The two-dimensional image display screen 4100 displays an outline diagram of a scanning locus when the tomographic image displayed in the tomographic image display screen 4200 is acquired as an arrow 4102 in a superimposed manner. Further, a grid 4103 to be a base of sector data described later is displayed in a superimposed manner.

A layer thickness map 4300, a comparative layer thickness map 4400, sector layer thickness data 4500, and comparative sector layer thickness data 4600 are also displayed. These are described below in detail.

Layer Thickness Map

Figure 1A:
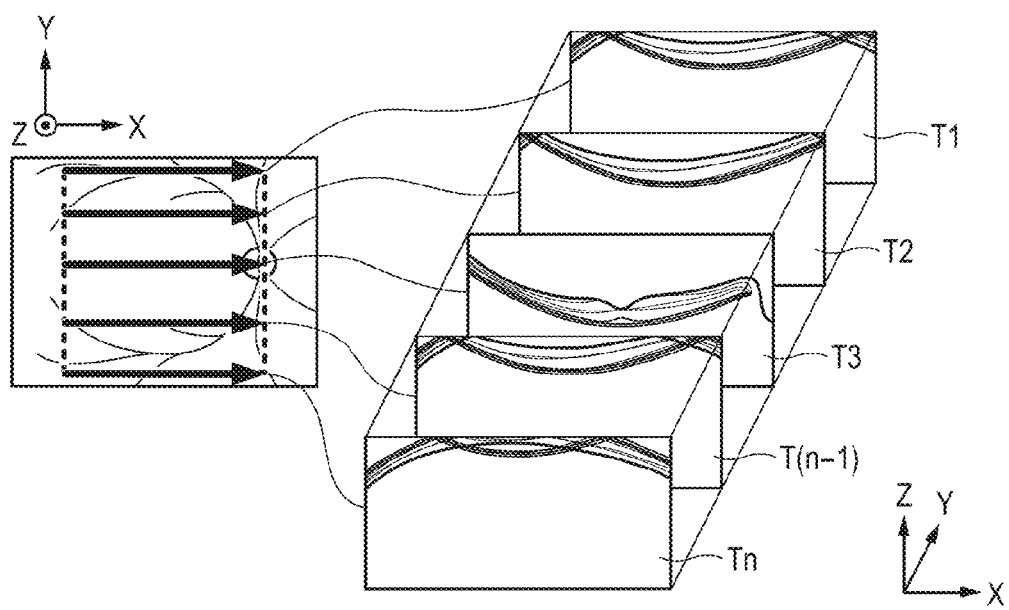
FIGS. 1A, 1B and 1C are explanatory diagrams of a layer thickness map according to the present invention.

The layer thickness map of this embodiment is described with reference to FIGS. 1A to 1C.

Figure 5:
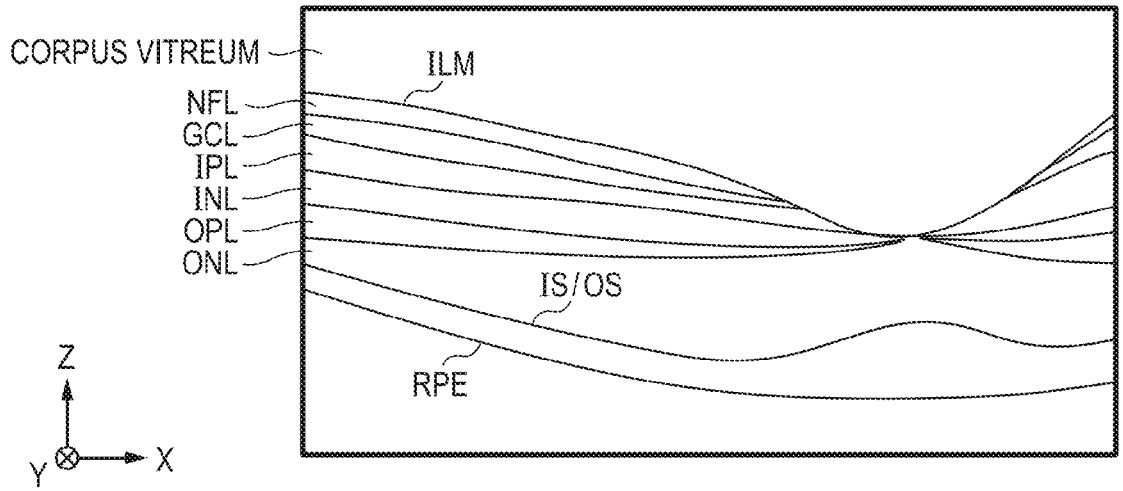
FIG. 5 is an explanatory diagram of a retina structure of a human eye.

Here, as illustrated in FIG. 5, the human retina includes a corpus vitreum, an internal limiting membrane (ILM), a nerve fiber layer (NFL), a ganglion cell layer (GCL), an inner plexiform layer (IPL), an inner nuclear layer (INL), an outer plexiform layer (OPL), an outer-nuclear layer (ONL), a structure called photoreceptor inner segment/outer segment junction-retinal pigmented epithelium (IS/OS-RPE), and the like. Further, it is known that, for example, a layer thickness distribution called a ganglion cell complex (GCC, a trademark) in which NFL, GCL, and IPL are combined is important for diagnosis of glaucoma. Image analysis data called the layer thickness map is effective for the above-mentioned diagnosis. This displays a variation of thickness of a specific layer as a color variation.

The layer thickness map is described with reference to FIGS. 1A to 1C. Here, there is described the layer thickness map generated in a case of volume data of the tomographic image including a folded image illustrated in FIG. 1A. FIG. 1C is an outline diagram of the layer thickness map in a case where the significant area as a feature of the present invention is not set. There are displayed a two-dimensional image 4301, the layer thickness map 4300, and a color scale 4310 showing colors corresponding to the layer thicknesses. The inside of the area of the layer thickness map 4300 shows layer thicknesses based on a result of layer thickness analysis of a specific layer with colors corresponding to the color scale 4310. Thus, the user can observe a distribution of the layer thicknesses easily and intuitively so as to efficiently perform the diagnosis. Further, in FIG. 1C, the filling color is a translucent color and is displayed in a superimposed manner on the two-dimensional image 4301.

However, it is difficult to analyze the layer structure in a part of the tomographic image having the folded image. Therefore, the display of the layer thickness may be 0 μm in a periphery of the layer thickness map 4300, or discontinuity may occur in the data, which causes low reliability. When the user is provided with such data, the user may be required to check every time whether the layer thickness of the part is abnormal or the layer thickness calculation has failed due to a folded image, which may lower analysis efficiency.

Figure 1B:
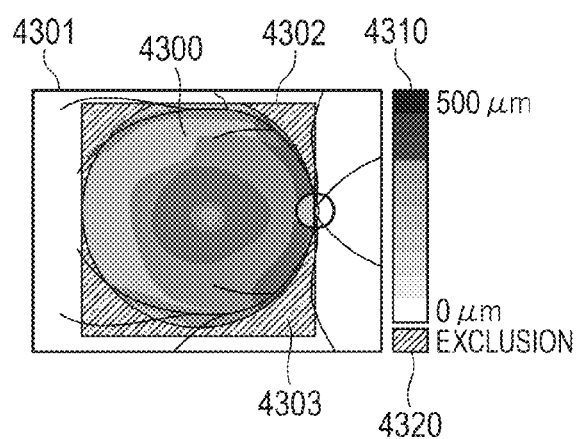
Figure 1C:
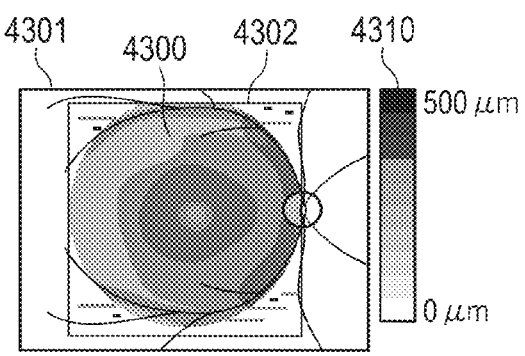

In contrast, FIG. 1B illustrates a layer thickness map in a case where the significant area is set as the feature of the present invention. There are displayed the two-dimensional image 4301, the layer thickness map 4300, the color scale 4310 indicating colors corresponding to layer thicknesses, and an indicator 4320 indicating an area (masking area) other than the significant area. As illustrated by a masking area 4303 in the layer thickness map 4300, a folded area is distinguished and clearly displayed to the user so that the user can easily recognize only reliable data. Therefore, the user is not required to check a failure in the layer thickness calculation due to the folded image, but can pay attention to only a part having a real abnormality so that analysis efficiency can be improved.

Figure 6A:
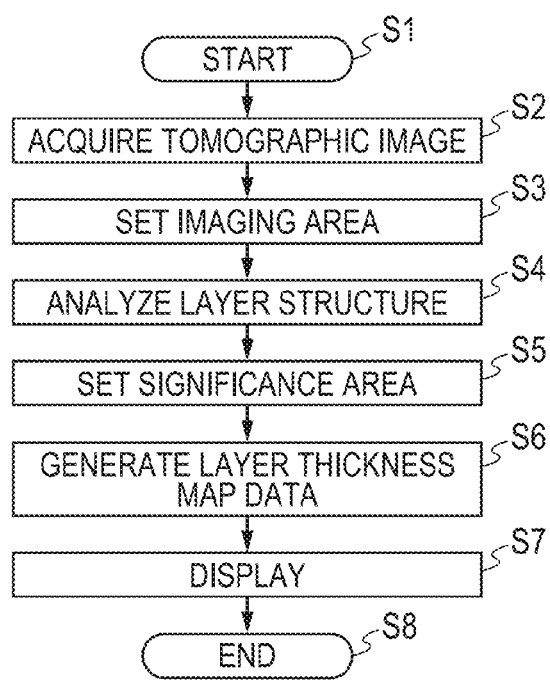
FIG. 6A is a flowchart for generating the layer thickness map according to the present invention.
Figure 6B:
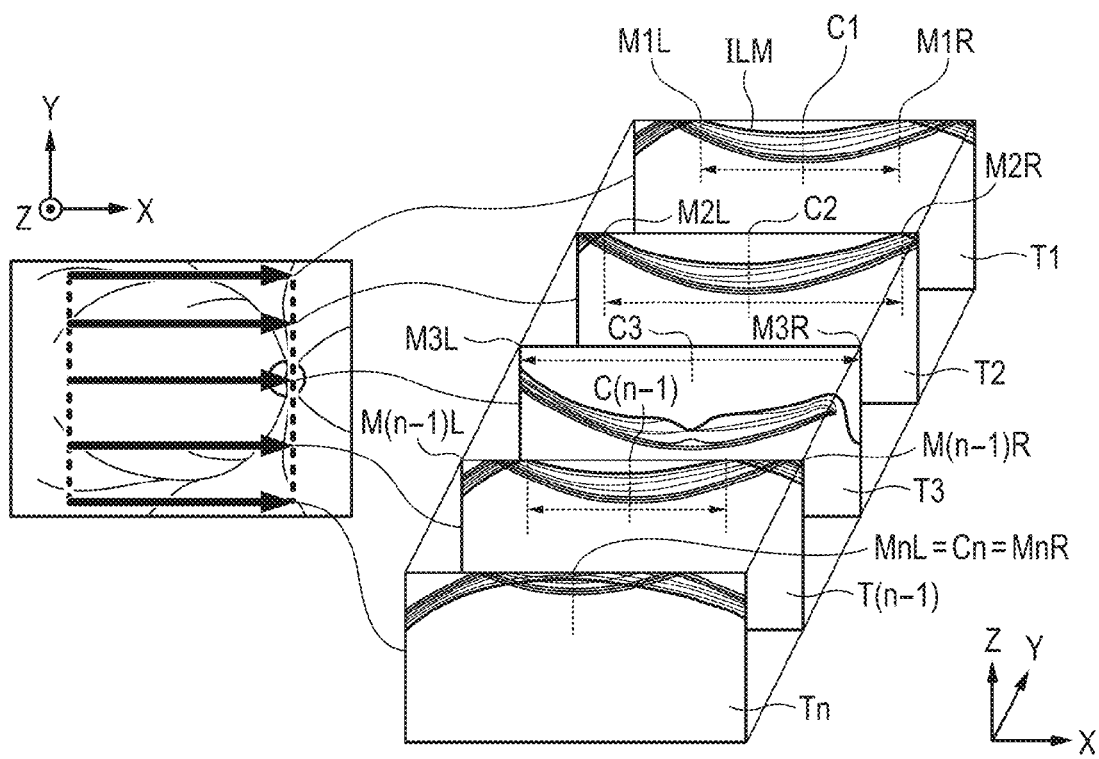
FIGS. 6B and 6C are explanatory diagrams of a method of determining a significant area according to the present invention.
Figure 6C:
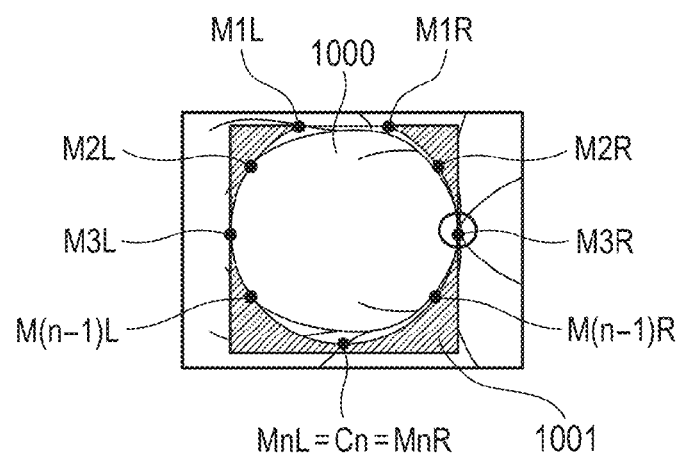

Next, with reference to FIGS. 6A to 6C, there is described a flow of generating the layer thickness map according to this embodiment. First, after starting the flow in Step S1, the acquisition portion 900 acquires volume data of the tomographic image in Step S2, and the tomographic image generation portion 330 generates the tomographic image.

Next, in Step S3, the imaging area identifying portion 931 sets the imaging area on the tomographic image generated in Step S2. Here, as described above, the imaging area means an area for cutting a part from the periodical tomographic image generated by Fourier transform when the tomographic image is generated, and is an outer frame of the tomographic image display screen 4200 and an outer frame 4302 of the layer thickness map 4300 in the report screen 4000. In other words, the imaging area is equivalent to the image display area that is an area in which the tomographic image is displayed on the monitor 928.

Next, in Step S4, the layer structure analysis portion 932 analyzes the layer structure of the object to be inspected. In the layer structure analysis, each layer can be distinguished by utilizing the fact that signal intensities are different among layers because the layers nave different reflectances.

Next, in Step S5, the significant area determination portion 933 identifies the significant area. The significant area determination portion 933 sets the significant area based on a positional relationship between the specific layer and the imaging area. Here, specific operation of the significant area determination portion is described with reference to FIG. 6B. Here, there is described an example in which the GCC is an object tor measuring the layer thickness, and the positional relationship between the ILM and the imaging area upper side is calculated, T1, T2, T3, . . . , T(n-1), and Tn indicate tomographic images constructing the volume data. Here, the tomographic image T1 is paid attention to. First, the significant area determination portion 933 sets a center position C1 of the tomographic image in the left and right directions in the diagram. Next, intersections between the ILM and the imaging area upper side are determined in the left and right directions in the diagram from the center position C1. Further, coordinates of the intersections in the left and right directions are denoted by M1L and M1R. The area between M1L and M1R is the significant area without a folded image and is an area in which a reliable layer thickness can foe obtained. On the other hand, in the area outside the significant area, a folded image is generated and causes a double image with a normal image. Therefore, reliability of the obtained layer thickness may be low. Determination of the intersection between the ILM and the imaging area upper side is equivalent to, for example, determination of a point at which a predetermined layer (for example, ILM) included in the tomographic image contacts with the periphery (for example, the upper end) of the image display area that is an area in which the tomographic image is displayed in the monitor 928.

Using the same method as described above, intersections M2L, M3L, . . . , MnL and M2R, M3R, . . . , MnR between the upper side and the ILM are determined tor individual tomographic images. Here, when the focused layer and the upper side of the imaging area have no intersection like the tomographic image T3, left and right boundaries of the imaging area are set as the intersections M3L and M3R, respectively. In addition, when the focused layer is the folded image in the entire area like the tomographic image Tn, the layer structure analysis portion 932 cannot distinguish the ILM, and therefore the center point Cn is set as the intersections MnL and MnR. After setting the intersections for all the tomographic images constituting the volume data as described above, the intersections are connected so that a significant area 1000 and an area 1001 outside the significant area can be obtained as illustrated in FIG. 6C.

After the significant area determination portion 933 identifies the significant area in Step S5 by the above-mentioned method, the process proceeds to Step S6. Then, the analyzed image generation portion 934 generates the layer thickness map data based on the layer structure obtained in Step S4 and the significant area obtained in Step S5. Specifically, the thickness of the specific layer, namely the GCC is measured based on the layer structure for A-scan data in the significant area, and color data corresponding thereto is held. On the other hand, color data or pattern indicating the masking area is held for the A-scan data outside the significant area. After generating the layer thickness map data in Step S6, the display on the report screen 4000 is performed in Step S7 and the process is finished in Step S8.

By generating the layer thickness map by the above-mentioned flow, the user can observe the layer thickness map useful for ophthalmological diagnosis in a state where it is possible to instantaneously discriminate an area in which the folded image may affect the layer thickness analysis data. Thus, analysis efficiency can be improved.

Here, the layer thickness measurement is not performed for the masking area in Step S6 described above, but it is possible to perform the layer thickness measurement also for the masking area. In this case, the color data is held also for the masking area, and the color data or pattern indicating the masking area is superimposed thereon in a translucent manner. An example of this display is illustrated in FIG. 7A. Using the layer thickness map as illustrated in FIG. 7A, the user can confirm the layer thickness distribution in the entire imaging area and can distinguish a reliable significant area.

In addition, the masking area may not be filled with a specific color or pattern. As illustrated in FIG. 7B, only a boundary line 4304 thereof may be drawn in the layer thickness map as a display that the user can distinguish.

In the above description of the layer thickness map, the layer thickness of the GCC is exemplified, but it is possible to use the layer other than the GCC. In the ophthalmological diagnosis, the IS/OS-RPE layer is also paid attention to in addition to the GCC in many cases. This is because the observation of presence or absence of choroidal neovascularization in the RPE is effective for diagnosis of age-related macular degeneration or the like. Therefore, it is desired that a layer to be analyzed can be selected by a layer selection unit (not shown).

A method of identifying the significant area in this case is described with reference to FIG. 8. When the significant area is set for the IS/OS-RPE layer, according to the above-mentioned flow, an intersection 1100 between an IS/OS line and the imaging area is determined, and the significant area is set therefrom. However, between the intersection 1100 and an intersection 1101 between the IS/OS line and the folded image of ILM, the folded image crosses the normal tomographic image. Therefore, it is difficult to analyze the layer thickness. Therefore, it is desired to set the significant area based on the intersection 1101 between the IS/OS line and the folded image of the ILM. Here, an example of a method of determining the intersection 1101 is described.

First, an intersection 1102 between the ILM and the imaging area upper side is determined. Next, an intersection 1103 with the IS/OS line at the same X position as the intersection 1102 is determined. Further, an intersection 1104 between the Z position of the intersection 1103 and the ILM is determined. Here, each layer of the retina viewed locally is approximated as a straight line, and it is supposed that the layers are parallel to each other. Then, a distance 1106 in the X direction between the intersection 1102 and the intersection 1101 is approximately a half of a distance 1105 in the X direction between the intersection 1102 and the intersection 1104. By the calculation described above, the intersection 1101 can be estimated. By setting the significant area by the above-mentioned method for the layer thickness analysis without the ILM, it is possible to effectively eliminate an area in which the folded image may affect the layer thickness measurement and to provide the user with the significant area enlarged as much as possible.

Layer Thickness Map NDB

Next, the comparative layer thickness map 4400 is described with reference to FIGS. 9A to 9E. The comparative layer thickness map displays a result of comparison between a reference layer thickness map and the above-mentioned layer thickness map. Here, the reference layer thickness map is a layer thickness map of a typical human eye retina, a past layer thickness map of the same patient, or a layer thickness map of the other of the left and right eyes of the same patient, and is scored in advance in the memory portion 926.

Figure 9A:
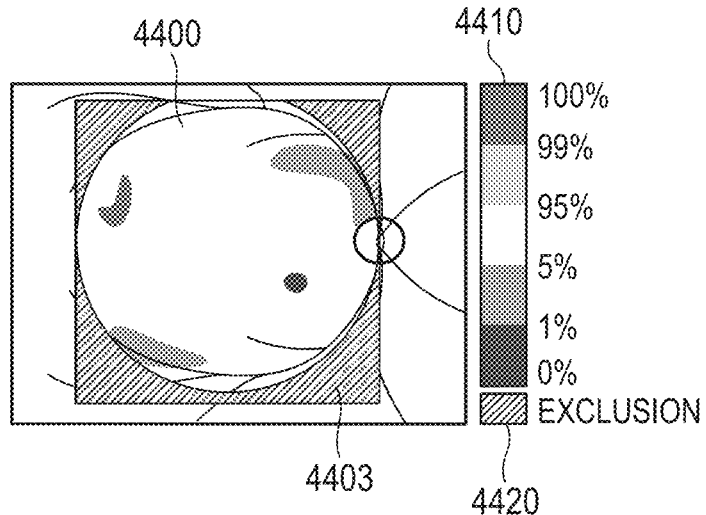
FIGS. 9A, 9C, 9D and 9E are explanatory diagrams of a comparative layer thickness map according to the present invention.

A structure of the comparative layer thickness map is described with reference to FIG. 9A. The comparative layer thickness map 4400, a color scale 4410 indicating colors corresponding to comparative layer thickness data, and an indicator 4420 indicating an area (masking area) other than the significant area are displayed.

Also in the comparative layer thickness map 4400, as illustrated by a masking area 4403 similarly to the layer thickness map, the folded area is distinguished and clearly displayed to the user so that the user can easily recognize only reliable data.

Figure 9B:
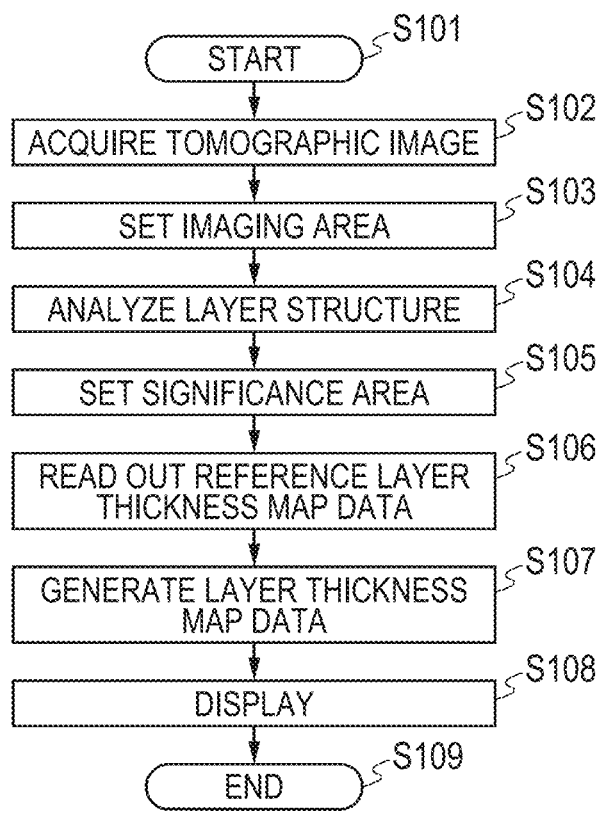
FIG. 9B is a flowchart for generating the comparative layer thickness map according to the present invention.
Figure 9C:
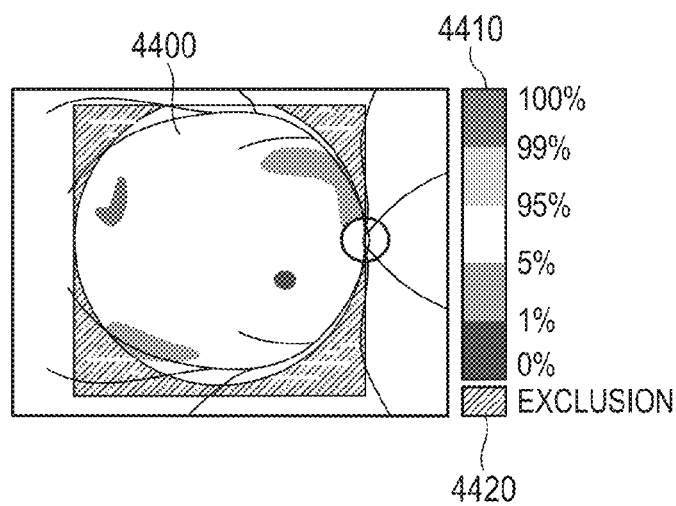

Next, with reference to FIG. 9B, a flow of generating the comparative layer thickness map is described. Operation from Step S101 to Step S105 is the same as the operation from Step S1 to Step S5 of the layer thickness map described above, and description thereof is omitted.

After setting the significant area in Step S105, the analyzed image generation portion 934 retrieves the reference layer thickness map from the memory portion 926 in Step S106. In Step S107, the analyzed image generation portion 934 generates the layer thickness map from the layer structure generated in Step S104, and a ratio to the reference layer thickness is calculated based on the thickness of the reference layer thickness map retrieved in Step S106 with respect to the layer thickness at each position, to thereby generate data to be the base of the comparative layer thickness map.

Figure 9D:
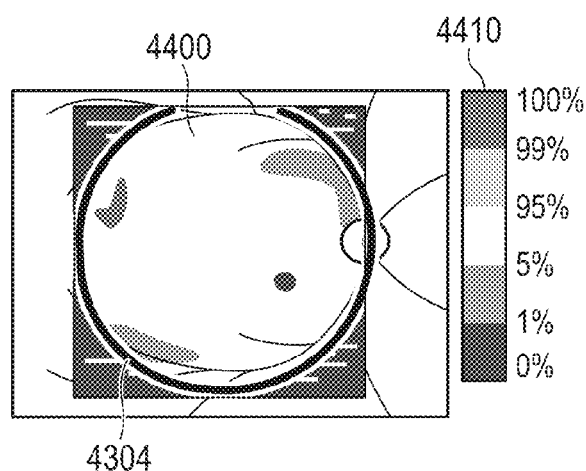
Figure 9E:
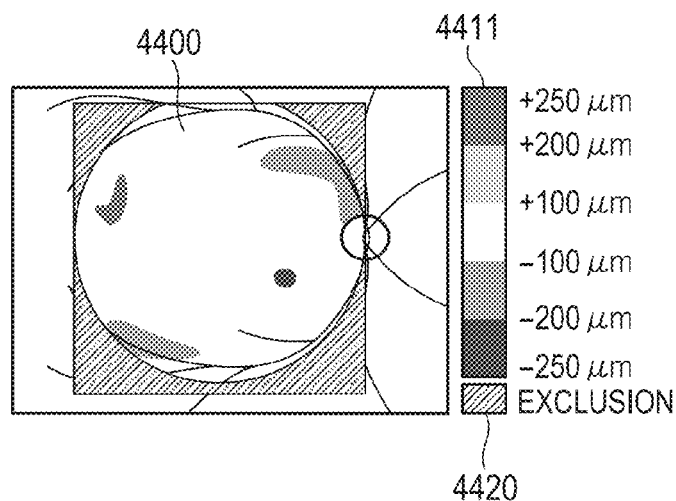

Then, combined with the significant area generated in Step S105, the comparative layer thickness map as the color map similar to the above-mentioned layer thickness map is generated. An example of the comparative layer thickness map is illustrated in FIG. 9A. FIG. 9A illustrates an example in which the masking area is filled with a pattern, but it is possible to adopt a display method of superimposing a translucent pattern on the color data (FIG. 9C) similarly to the layer thickness map described above or a method of displaying only the boundary line (FIG. 9D). In the above description, there is described an example in which ratio data to the reference layer thickness data is generated, but it is possible to generate and display difference amount data as illustrated in FIG. 9E.

Further, as data used as the reference layer thickness data, there is layer thickness data of healthy eyes, past inspection data of the same eye, data of the other of the left and right eyes of the same patient, or the like. The layer thickness data of healthy eyes is called normative data base (NDB) and is layer thickness data of healthy eyes of different races and ages. By comparing this NDB with the layer thickness of the patient, it is possible to easily check an abnormality in the layer thickness of the patient. In particular, it is known that noting the layer thickness of the GCC is very effective for diagnosis of glaucoma.

In addition, the past inspection data of the same eye is useful for follow-up observation and enables the examiner to easily check aging of the layer thickness. Therefore, the past inspection data of the same eye is used for diagnosis of progress situation of glaucoma. Further, using the other of the left and right eyes of the same patient as the reference layer thickness data is useful in a case where one of left and right eyes has an abnormality.

As described above, also in the comparative layer thickness map, the significant area is set and provided to the user, and hence the user can observe the comparative layer thickness map useful for ophthalmological diagnosis in a state where reliable data can be easily discriminated without a folded image. Therefore, analysis efficiency can be improved.

Sector Data

Figure 10A:
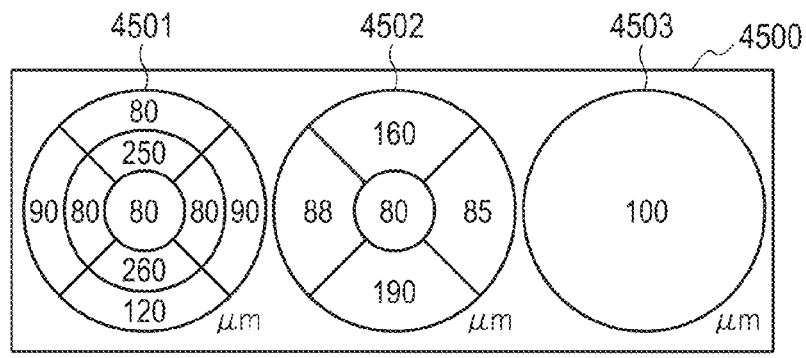
FIGS. 10A, 10C, 10D, 10E, 10F and 10G are explanatory diagrams of sector layer thickness data according to the present invention.

Next, with reference to FIGS. 10A to 10G, a structure of the sector layer thickness data is described. In FIG. 10A, sector layer thickness data 4501 indicates a layer thickness average value in each sector when an object to be measured is divided into the above-mentioned grid 4103. In FIG. 10A, sector layer thickness data 4502 indicates a layer thickness average value in each sector when a plurality of adjacent sector areas are combined. In FIG. 10A, sector layer thickness data 4503 indicates a layer thickness average value in the sector when all the sector areas are combined.

Figure 10B:
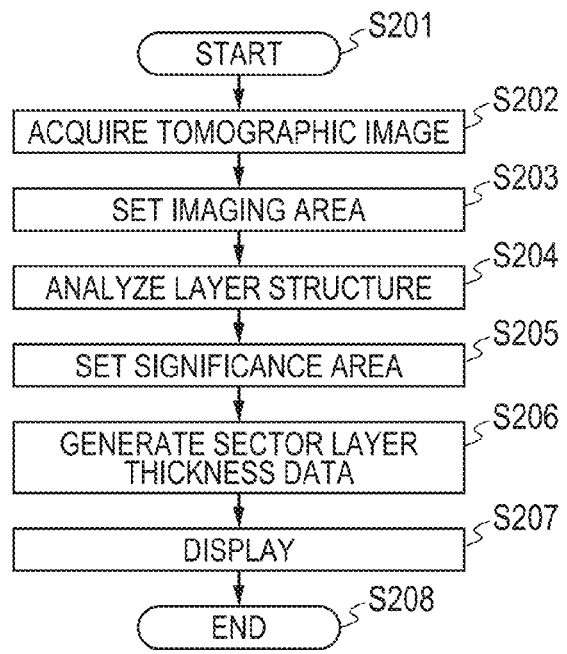
FIG. 10B is a flowchart for generating the sector layer thickness data.

Next, with reference to FIG. 10B, an operation flow of generating and displaying the sector layer thickness data is described. Operation from Step S201 to Step S205 is the same as the operation from Step S1 to Step S5 of the layer thickness map described above, and description thereof is omitted. After setting the significant area in Step S205, the analyzed image generation portion 934 generates sectors in Step S206 based on the layer structure obtained in Step S204 and the data of the grid 4103, and calculates the layer thickness average value of each sector from the thickness data of all layers constructing the sector. Next, the analyzed image generation portion 934 generates the sector layer thickness data in Step S206 based on information of the significant area generated in Step S205, and displays the sector layer thickness data in Step S207.

Figure 10C:
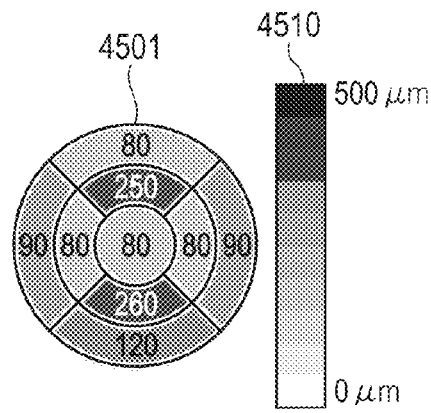
Figure 10D:
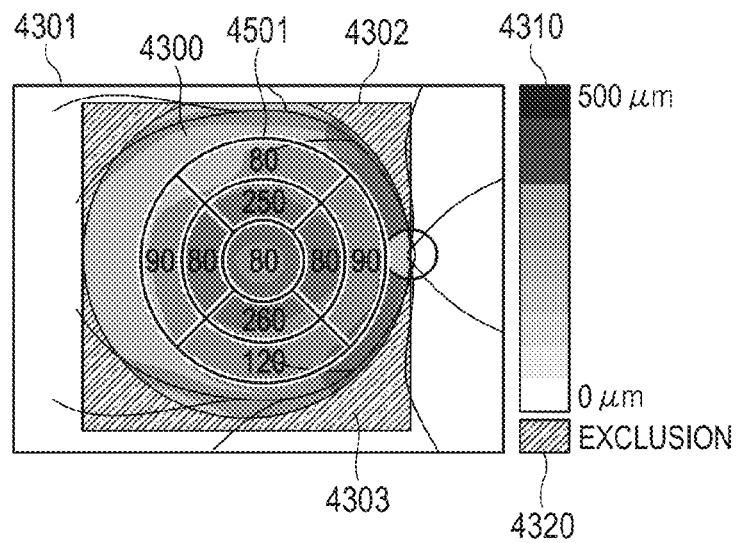

Here, a method of displaying the sector layer thickness data is not limited to the display of only numerals as illustrated in FIG. 10A. For instance, as illustrated in FIG. 10C, it is possible to display each sector filled with color corresponding to the layer thickness. In addition, as illustrated in FIG. 10D, it is possible to display the sector layer thickness data so as to superimpose on a two-dimensional image or the layer thickness map described above.

Figure 10E:
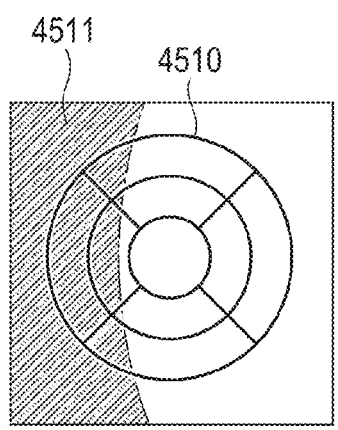
Figure 10F:
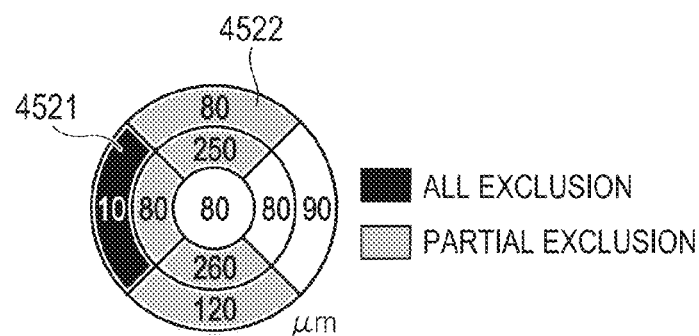
Figure 10G:
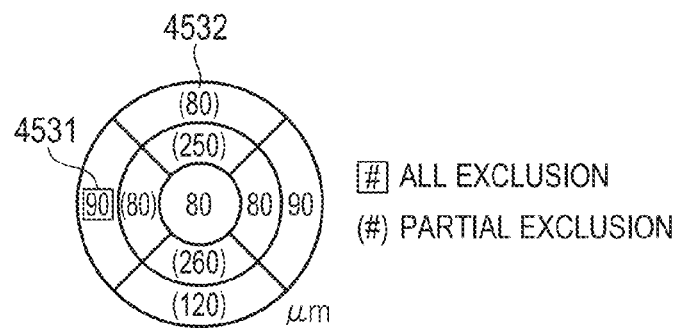

Next, there is described a case where the sector area and the area (masking area) outside the significant area are overlapped. When a masking area 4511 overlaps a sector area 4510 as illustrated in FIG. 10E, the display is performed in a form as illustrated in FIG. 10F or 10G. Then, the user can instantaneously distinguish data that may affect the layer thickness data due to the folded image from other data. A sector 4521 in FIG. 10F indicates by its color information in the sector that the entire sector area is included in the masking area. In addition, a sector 4522 in FIG. 10F indicates by its color information in the sector that a part of the sector area is overlapped with the masking area.

Here, a sector 4521 and a sector 4522 are displayed in different colors, but may be displayed in the same color when it is sufficient to distinguish whether or not there is an overlap with the masking area. Using this display method, the user can distinguish at a glance whether or not there is a possible influence of the folded image. In addition, FIG. 10G illustrates an example in which the numeral display form is changed. A sector 4531 in FIG. 10G suggests that the entire sector area is included in the masking area by using enclosed numeral for indicating the layer thickness data in the sector. In addition, a sector 4532 in FIG. 10G suggests that a part of the sector area is overlapped with the masking area by using numeral in parentheses for indicating the layer thickness data in the sector. Using thus display method, it is possible to provide easy-to-see sector layer thickness data even in a case where the display is performed in a form of superimposing on the two-dimensional image or the layer thickness map.

Here, there is described an example in which when the sector layer thickness average value is calculated in Step S206, the average value is calculated from the thickness data of all layers constructing the sector. However, it is possible to calculate the average value by using only the layer thickness data in the sector and in the significant area. In this way, it is possible to eliminate an influence of the folded image to the layer thickness data, and hence reliable sector layer thickness data can be obtained. Further, in this case, it is desired to inform the user that the data used for calculation is selected by the masking area using the display method as illustrated in FIG. 10F or 10G.

Sector NDB

Next, the comparative sector layer thickness data 4600 is described with reference to FIGS. 11A and 11B. Here, sector layer thickness data to re a reference is sector layer thickness data of a typical human eye retina, past sector layer thickness data of the same patient, or sector layer thickness data of the other of the left and right eyes of the same patient, and is stored in advance in the memory portion 926.

The comparative sector layer thickness data is described with reference to FIG. 11A. Ratios 4601 displayed as illustrated in FIG. 11A are obtained by comparing the sector layer thickness data indicating the layer thickness average value in each sector when dividing the object to be measured by the above-mentioned grid 4103 with the corresponding reference sector layer thickness data.

Figure 11A:
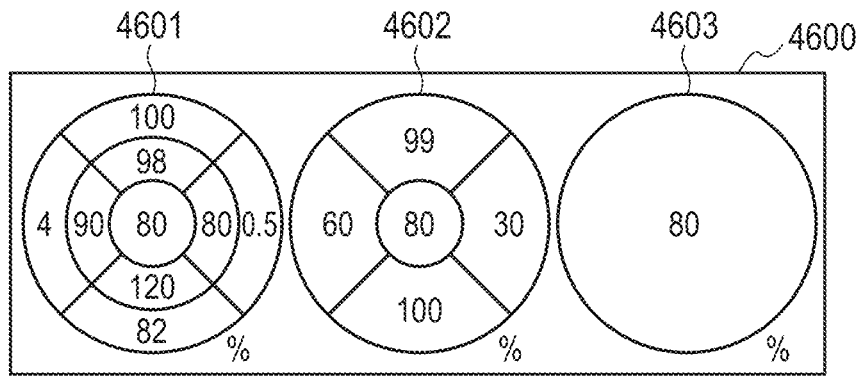
FIG. 11A is an explanatory diagram of comparative sector layer thickness data according to the present invention.
Figure 11B:
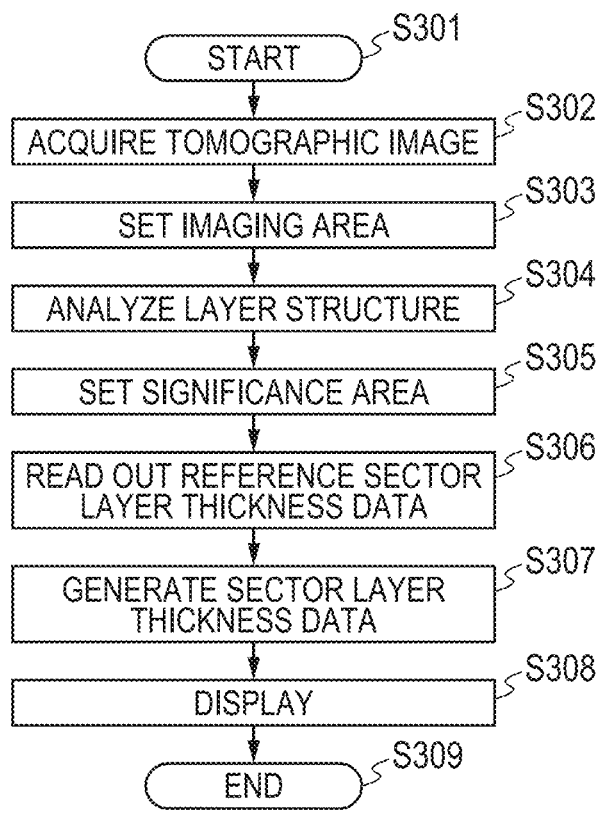
FIG. 11B is a flowchart for generating the comparative sector layer thickness data.

Ratios 4602 displayed as illustrated in FIG. 11A are obtained by comparing the sector layer thickness data indicating the layer thickness average value in each sector, when the plurality of adjacent sector areas are combined, with the corresponding reference sector layer thickness data. The ratio 4603 displayed as illustrated in FIG. 11A is obtained by comparing the sector layer thickness data indicating the layer thickness average value in the sector, when all the sector areas are combined, with the corresponding reference sector layer thickness data.

Next, an operation flow of generating and displaying the sector layer thickness data is described with reference to FIG. 11B. Operation from Step S301 to Step S305 is the same as the operation from Step S1 to Step S5 of the layer thickness map described above, and description thereof is omitted. After setting the significant area in Step S305, the analyzed image generation portion 934 retrieves the reference sector layer thickness data from the memory portico 926 in Step S306.

Next, the analyzed image generation portion generates the sector layer thickness data in Step S307 similarly to S206 described above, and calculates a ratio to the reference layer thickness based on the thickness of the reference sector layer thickness data retrieved in S306 with respect to the layer thickness at each sector position, so as to generate data to be a base of the comparative sector layer thickness data. Then, combined with the significant area generated in Step S305, the comparative sector layer thickness data is generated. This data is displayed in Step S308.

Here, as the display method for the comparative layer thickness data, other than the method illustrated in FIG. 11A, there are a display method of filling the sector area with a color corresponding to the calculated value as illustrated in FIG. 10C and a display method of superimposing on the two-dimensional image or the layer thickness map as illustrated in FIG. 10D.

In addition, also in a case where the masking area is overlapped with the sector area, there are a method of changing the color information in the sector as illustrated in FIG. 10F and a method of changing a display form of characters as illustrated in FIG. 10G depending on the positional relationship between the sector area and the masking area.

Here, as the display method for the comparative layer thickness data, other than the method illustrated in FIG. 11A, there are a display method of filling the sector area with a color corresponding to the calculated value as illustrated in FIG. 10C and a display method of superimposing on the two-dimensional image or the layer thickness map as illustrated in FIG. 10D.

In the above description, there is described an example in which the ratio data to the reference sector layer thickness data is generated. However, it is possible to generate and display the difference amount data similarly to the comparative layer thickness map described above.

Further, as the data to be used as the reference layer thickness data, there are layer thickness data of healthy eyes, past inspection data of the same eye, data of the other of the left, and right eyes of the same patient, and the like similarly to the comparative layer thickness map.

Further, there is described the example in which when the sector layer thickness average value is calculated in Step S306, the average value is calculated from the thickness data of all layers constructing the sector. However, as described above, it is possible to calculate the average value by using only the layer thickness data in the sector and in the significant area.

As described above, in the layer thickness map and the sector layer thickness data, the user is provided with the information on presence or absence of a possible influence of the folded image, and hence the user can pay attention to a lesioned part of the eye to be inspected so that analysis efficiency can be improved.

As described above, according to one embodiment of the present invention, even when the object to be inspected includes a plurality of layers, it is possible to provide the user with an appropriate layer thickness of each layer. Further, by using colors or a boundary line for the display method in the layer thickness map, the user can easily recognize the area in which the folded image may affect the layer thickness analysis data.

In addition, according to one embodiment of the present invention, by using characters and colors for the display method in the sector layer thickness data, the user can easily recognize the area in which the folded image may affect the layer thickness analysis data.

Further, according to one embodiment of the present invention, because an influence of the folded image to the sector layer thickness data can be eliminated, reliability of the sector layer thickness data can be improved.

Other Embodiment

Further, the present invention can also be realized, by performing the following processing. That is, the processing involves supplying software (program) for realizing the functions of the above-mentioned embodiment to a system or an apparatus via a network or various storage media and causing a computer (or a CPU, an MPU, or the like) of the system or the apparatus to read and execute the program.

The present invention is not limited to the above-mentioned embodiment and can be variously modified or changed within the scope not departing from the spirit of the present invention. For example, in the above-mentioned embodiment, the case where an object to be inspected is an eye has been described, but the present invention can also be applied to objects to be measured such as a skin and an organ except an eye. In this case, the present invention has an aspect as medical equipment such as an endoscope except an ophthalmologic device. Therefore, it is desired that the present invention be understood as an optical tomographic imaging apparatus exemplified by an ophthalmologic device, and the eye to be inspected be understood as one aspect of the object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-096400, filed May 1, 2013, which is hereby incorporated by reference herein in its entirety.

The invention claimed is:

1. An image processing apparatus comprising:
   an acquisition unit configured to acquire a plurality of tomographic images of an eye to be inspected;
   a specification unit configured to specify an area of a tomographic image among the plurality of tomographic images, on which a folded image is generated; and
   a display control unit configured to control a display unit to display (1) a layer thickness map based on the plurality of tomographic images with (2) data indicating the area on which the folded image is generated,
   wherein the data indicating the area on which folded image is generated is superimposed on the layer thickness map, and
   wherein the display control unit controls the display unit to display the layer thickness map with a color and to display the data indicating the area on which the folded image is generated by a color different from the color of the layer thickness map.

2. An image processing apparatus according to claim 1, wherein the specification unit specifies the area on which the folded image is generated, based on (1) a layer obtained from each of the plurality of the tomographic images and (2) a position where an optical path length of an optical coherence tomography measuring beam is equal to an optical path length of an optical coherence tomography reference beam.

3. An image processing apparatus according to claim 1, wherein the layer thickness map includes a thickness map concerning a specific layer of a fundus of the eye to be inspected.

4. An image processing apparatus according to claim 1, further comprising a memory unit configured to store a reference layer thickness concerning a specific layer,
   wherein the layer thickness map includes one of a ratio and a difference amount of the layer thickness of a specific layer of the fundus of the eye to be inspected corresponding to the reference layer thickness.

5. An image processing apparatus comprising:
   an acquisition unit configured to acquire a plurality of tomographic images of an eye to be inspected;
   a specification unit configured to specify an area of a tomographic image among the plurality of tomographic images, on which a folded image is generated; and
   a display control unit configured to control a display unit to display a layer thickness map based on the plurality of tomographic images with data indicating the area on which the folded image is generated,
   wherein the data indicating the area on which folded image is generated is superimposed on the layer thickness map, and
   wherein the display control unit controls the display unit to display, as the data indicating the area on which the folded image is generated, a boundary line between the area on which the folded image is generated and an area on which the folded image is not generated.

6. An image processing apparatus comprising:
   an acquisition unit configured to acquire a plurality of tomographic images of an eye to be inspected;
   a specification unit configured to specify an area of a tomographic image among the plurality of tomographic images, on which a folded image is generated;
   a calculation unit configured to calculate data based on a layer thickness concerning a specific layer of the eye to be inspected in each of the plurality of the tomographic images, for each of sector areas obtained by dividing the eye to be inspected by a predetermined grid;
   a display control unit configured to control a display unit to display analyzed image data including the predetermined grid and the data based on the layer thickness,
   wherein the display control unit controls a display form of the analyzed image data, based on a positional relationship between the sector areas and the area on which the folded image is generated.

7. An image processing apparatus according to claim 6, further comprising a memory unit configured to store a reference layer thickness concerning the specific layer,
   wherein the data based on the layer thickness includes one of a ratio and a difference of the layer thickness concerning the specific layer for the reference layer thickness data.

8. An image processing apparatus according to claim 6, wherein the display control unit controls the display unit to display, as a numeral, data based on the layer thickness corresponding to a sector area, and changes a display form of the numeral between the sector area including the area on which the folded image is generated and the sector area including an area on which the folded image is not generated.

9. An image processing apparatus according to claim 6, wherein the display control unit controls the display unit to display the data based on the layer thickness by colors different between the sector area including the area on which the folded image is generated and the sector area including an area on which the folded image is not generated.

10. An image processing apparatus according to claim 6, wherein the calculation unit calculates the data based on the layer thickness, based on only the layer thickness value included in an area on which the folded image is not generated, among a plurality of layer thickness values included in the sector area.

11. A control method for an image processing apparatus, the control method comprising:
acquiring a plurality of tomographic images of an eye to be inspected;
specifying an area of a tomographic image among the plurality of tomographic images, on which a folded image is generated; and
controlling the display unit to display (1) a layer thickness map based on the plurality of tomographic images with (2) data indicating the area on which the folded image is generated,
wherein the data indicating the area on which folded image is generated is superimposed on the layer thickness map, and
wherein the controlling controls the display unit to display the layer thickness map with a color and to display the data indicating the area on which the folded image is generated by a color different from the color of the layer thickness map.

12. A non-transitory tangible medium having recorded thereon a program for causing a computer to perform steps of the control method according to claim 11.

13. An image processing apparatus according to claim 6, wherein the data based on the layer thickness includes an average value of the layer thicknesses in each of the sector areas.

14. An image processing apparatus according to claim 8, wherein the data based on the layer thickness includes an average value of the layer thicknesses in each of the sector areas.

15. An image processing apparatus according to claim 9, wherein the data based on the layer thickness includes an average value of the layer thicknesses in each of the sector areas.

16. An image processing apparatus according to claim 10, wherein the data based on the layer thickness includes an average value of the layer thicknesses in each of the sector areas.

17. An image processing apparatus comprising:
an acquisition unit configured to acquire a tomographic image of an object to be inspected;
a determination unit configured to determine a significant area and a non-significant area based on a positional relationship between (1) a periphery of an image display area in which the tomographic image is displayed and (2) the tomographic image;
a generation unit configured to generate a layer thickness map based on a specific layer of the tomographic image; and
a display control unit configured to control a display unit to display the layer thickness map generated by the generation unit to enable the significant area and the non-significant area to be distinguished by use of color based on a determination result by the determination unit.

18. An image processing apparatus according to claim 17, wherein the generation unit generates the thickness map without using the specific layer in the non-significant area.

19. An image processing apparatus according to claim 17, wherein the specific layer is a specific layer of a fundus of the eye to be inspected.

20. An image processing apparatus comprising:
an acquisition unit configured to acquire a tomographic image of an object to be inspected;
a determination unit configured to determine a significant area and a non-significant area based on a positional relationship between (1) a periphery of an image display area in which the tomographic image is displayed and (2) the tomographic image;
a generation unit configured to generate a layer thickness map, based on a specific layer of the tomographic image; and
a display control unit configured to control a display unit to display the layer thickness map generated by the generation unit to enable the significant area and the non-significant area to be distinguished by a boundary line drawn on a periphery of the significant area.

21. An image processing apparatus according to claim 1, wherein the image processing apparatus comprises a processor that executes a program so as to function as units comprising (a) the acquisition unit, (b) the specification unit, and (c) the display control unit.

22. An image processing apparatus according to claim 5, wherein the image processing apparatus comprises a processor that executes a program so as to function as units comprising (a) the acquisition unit, (b) the specification unit, and (c) the display control unit.

23. An image processing apparatus according to claim 6, wherein the image processing apparatus comprises a processor that executes a program so as to function as units comprising (a) the acquisition unit, (b) the specification unit, (c) the calculation unit, and (d) the display control unit.

24. An image processing apparatus comprising:
an acquisition unit configured to acquire data designating an area on which a folded image generates on a plurality of tomographic images of an eye to be inspected; and
a display control unit configured to control a display unit to display, based on the data designating the area on which the folded image generates, a layer thickness map based on the plurality of tomographic images.

25. An image processing apparatus according to claim 24, wherein the display control unit changes a display form of the layer thickness map based on the data designating the area on which the folded image generates.

26. An image processing apparatus according to claim 24, wherein the tomographic images are tomographic images of a fundus of the eye to be inspected.

27. An image processing apparatus according to claim 26, wherein the layer thickness map is generated based on a layer thickness of a predetermined layer included in each of the plurality of the tomographic images.

28. An image processing apparatus according to claim 27, wherein the layer thickness map is generated based on a ratio or a difference between the layer thickness of the predetermined layer and a reference layer thickness.

29. An image processing apparatus according to claim 27, further comprising a generation unit configured to generate the layer thickness map,
wherein the generation unit does not use the layer thickness of the predetermined layer in the area on which the folded image generates to generate the layer thickness map.

30. An image processing apparatus according to claim 24, wherein the acquisition unit acquires the data designating the area on which the folded image is generated based on 1) a layer obtained from each of the plurality of tomographic images, and 2) a position where an optical path length of a measuring beam of an Optical Coherent Tomography equates with an optical path length of a reference beam of the Optical Coherent Tomography.

31. An image processing apparatus according to claim 24, wherein the display control unit controls the display unit to display a mask formed based on the data designating the area on which the folded image generates, with the layer thickness map in a superimposed display form.

32. An image processing apparatus according to claim 24, wherein the display control unit controls, based on the data designating the area on which the folded image generates, the display unit to display the layer thickness map so that a layer thickness in the area on which the folded image generates is not displayed.

* * * * *